United States Patent
Koehler (10) Patent No.: US 8,690,834 B2
(45) Date of Patent: Apr. 8, 2014

(54) MEDICAL DEVICE WITH MULTI-PORT INFLATABLE HEMOSTATIC VALVE SYSTEM

(75) Inventor: Cleve Koehler, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 364 days.

(21) Appl. No.: 13/092,410

(22) Filed: Apr. 22, 2011

(65) Prior Publication Data

US 2012/0271116 A1 Oct. 25, 2012

(51) Int. Cl.
*A61M 5/178* (2006.01)

(52) U.S. Cl.
USPC ............... 604/167.03; 604/167.01; 604/264; 604/246

(58) Field of Classification Search
USPC ............. 604/167.03, 167.06, 164.01, 164.02, 604/167.01, 167.02, 246, 264, 256, 539, 604/908, 912, 99.04, 537; 606/167, 185
See application file for complete search history.

(56) References Cited

U.S. PATENT DOCUMENTS

| | | | |
|---|---|---|---|
| 4,875,897 A | 10/1989 | Lee | |
| 5,167,637 A | 12/1992 | Okada et al. | |
| 5,257,973 A | 11/1993 | Villasuso | |
| 5,269,772 A * | 12/1993 | Wilk | 604/284 |
| 5,354,271 A | 10/1994 | Voda | |
| 5,383,896 A | 1/1995 | Gershony et al. | |
| 5,814,026 A | 9/1998 | Yoon | |
| 5,891,113 A | 4/1999 | Quinn | |
| 5,919,183 A | 7/1999 | Field | |
| 6,099,506 A | 8/2000 | Macoviak et al. | |
| 6,217,555 B1 * | 4/2001 | Hart et al. | 604/167.01 |
| 6,352,520 B1 | 3/2002 | Miyazaki | |
| 6,352,521 B1 | 3/2002 | Prosl | |
| 6,623,426 B2 | 9/2003 | Bonadio et al. | |
| 7,025,741 B2 | 4/2006 | Cull | |
| 7,736,328 B2 | 6/2010 | Childers et al. | |
| 7,762,999 B2 | 7/2010 | Byrum | |
| 8,206,294 B2 * | 6/2012 | Widenhouse et al. | 600/210 |
| 2004/0167559 A1 * | 8/2004 | Taylor et al. | 606/185 |
| 2007/0078395 A1 | 4/2007 | Valaie | |
| 2009/0326468 A1 * | 12/2009 | Blier | 604/167.01 |

OTHER PUBLICATIONS

Gore & Associates, Inc, Product Information Sheet, Gore DrySeal Valve, 2010.

* cited by examiner

*Primary Examiner* — Aarti B Berdichevsky
*Assistant Examiner* — Laura Schell
(74) *Attorney, Agent, or Firm* — Buchanan Nipper (57) ABSTRACT

A medical device is provided having a hemostatic valve system that allows substantially leak-free passage of one or more medical interventional devices, such as a catheter, for insertion into a body vessel. The medical device comprises a hemostatic valve system and an elongate tubular member. The hemostatic valve system comprises a body, one or more pouches, and one or more disks.

20 Claims, 8 Drawing Sheets

MEDICAL DEVICE WITH MULTI-PORT INFLATABLE HEMOSTATIC VALVE SYSTEM

FIELD

The invention relates to medical devices. More particularly, the invention relates to medical devices, such as introducers, having a hemostatic valve system that allows substantially leak-free passage of one or more interventional devices, such as catheters, through the medical device for insertion into a body vessel.

BACKGROUND

Numerous procedures have been developed in modern medicine that require the percutaneous insertion of one or more interventional devices into the vascular system. Such procedures include, for example, percutaneous transluminal coronary angioplasty (PTCA), X-ray angiographic procedures, and the like.

The interventional devices intended for use in such procedures may be introduced into the vascular system by a variety of known techniques. In the widely used Seidinger technique, a surgical opening is made in a body vessel, such as an artery or vein, by a needle, and a wire guide is inserted into the body vessel through a bore in the needle. The needle is then withdrawn, leaving the wire guide in place. A dilator positioned within the lumen of an introducer device is then inserted over the wire guide and advanced into the body vessel. Once the introducer is positioned as desired within the body vessel, the dilator is withdrawn. A variety of medical devices, such as catheters, delivery systems, cardiac leads, and the like, can then be advanced through the introducer to a point of treatment in the body vessel.

In many cases, an introducer will include one or more hemostatic valve members (also referred to as check valves) for inhibiting leakage of bodily fluids, such as blood, through the introducer as an interventional device is inserted through or withdrawn from the introducer. In some cases, hemostatic valves that include an elastomeric component are used to minimize fluid leakage during these exchanges. These hemostatic valves that include an elastomeric component are dependent upon the ability of the elastomeric component to seal around the interventional devices to close any gaps created upon insertion or withdrawal of the device through the valve.

During procedures involving the percutaneous insertion of one or more interventional devices into the vascular system it is sometimes necessary or desirable to replace a previously-inserted interventional device with another interventional device of a different diameter, or even with an interventional device of a different type. Such exchanges are normally made over the wire guide, wherein the old device is withdrawn over the wire guide and the new device is inserted into the body vessel over the existing wire guide or a newly-inserted wire guide. In addition procedures, such as the placement of endovascular grafts, can involve interventional devices of relatively large diameters and/or simultaneous placement of multiple interventional devices through the introducer. These procedures present challenges in the efforts to inhibit leakage as conventional hemostatic valve members are not well-suited for such procedures. Thus, there is a need for improved hemostatic valves and medical devices that include such valves.

BRIEF SUMMARY OF THE DISCLOSURE

Medical devices that include a hemostatic valve system are described.

A first exemplary medical device comprises an elongate tubular member and a hemostatic valve system. The hemostatic valve system is disposed on the elongate tubular member and comprises a body and one or more pouches. The body comprises a proximal end, a distal end, a wall defining an interior and exteri- or surface, a chamber disposed between the proximal and distal ends, and a plurality of device ports disposed on the proximal end. The plurality of device ports extend through the wall and provide access to the chamber. The one or more pouches are disposed within the clamber and have a first unexpanded configuration and a second expanded configuration.

A second exemplary medical device comprises an elongate tubular member and a hemostatic valve system. The hemostatic valve system is disposed on the elongate tubular member and comprises a body, one or more pouches, and one or more disks. The body comprises a proximal end, a distal end, a wall defining an interior and exterior surface, a chamber disposed between the proximal and distal ends, and a plurality of device ports disposed on the proximal end defining arecess. The plurality of device ports extend through the wall and provide access to the chamber. The one or more pouches are disposed within the chamber and have a first unexpanded configuration and a second expanded configuration. The one or more disks are disposed within the recess and span the access provided by the one or more device ports.

A third exemplary medical device comprises an elongate tubular member and a hemostatic valve system. The hemostatic valve system is disposed on the elongate tubular member and comprises a body, a plurality of pouches, and one or more disks. The body comprises a proximal end, a distal end, a wall defining an interior and exterior surface, a chamber disposed between the proximal and distal ends, and a plurality of device ports disposed on the proximal end defining arecess. The plurality of device ports extend through the wall and provide access to the chamber. The plurality of pouches are disposed within the chamber and have a first unexpanded configuration and a second expanded configuration. The one or more disks are disposed within the recess and span the access provided by the one or more device ports.

Hemostatic valve systems independent of any other medical device are also described. An exemplary hemostatic valve system comprises a body, a plurality of pouches, and one or more disks. The body comprises a proximal end, a distal end, a wall defining an interior and exterior surface, a chamber disposed between the proximal and distal ends, and a plurality of device ports disposed on the proximal end defining a recess. The plurality of device ports extend through the wall and provide access to the chamber. The plurality of pouches are disposed within the chamber and have a first unexpanded configuration and a second expanded configuration. The one or more disks comprise a slit and are disposed within the recess and span the access provided by the plurality of device ports. The one or more disks are contained within the recess by a retaining ring.

DETAILED DESCRIPTION

The following detailed description and the appended drawings are provided to describe and illustrate exemplary embodiments of the invention for the purpose of enabling one of ordinary skill in the relevant art to make and use the invention. The description and drawings are not intended to limit the scope of the invention or its protection in any manner.

Throughout the specification, the terms "proximal" and "distal" are used to describe opposing axial ends of the particular elements or features being described. In addition, the term "device" refers to any device, object, apparatus, or structure, that supports, repairs, or replaces, a part of the body or a function thereof, or is configured to do the same, alone or in combination with other devices. Furthermore, the term "hemostatic" referres to providing complete, substantial, or partial stoppage of blood flow.

FIGS. 1 through 6 illustrate a medical device 100 comprising a hemostatic valve system 102 and an elongate tubular member 110. The elongate tubular member 110 has proximal and distal ends, and defines an interior lumen 111. The hemostatic valve system 102 has proximal 104 and distal 106 ends and a longitudinal axis 108. The distal end 106 of the hemostatic valve system 102 is disposed on and fixedly attached to the proximal end of the elongate tubular member 110. The hemostatic valve system 102 can be, however, integrally formed with the elongate tubular member 110 or releasably attached to the elongate tubular member 110.

The hemostatic valve system 102 comprises a body 130 having a wall 184 with interior 180 and exterior 182 surfaces. The wall 184 defines an interior chamber 186 that extends between the proximal 104 and distal 106 ends of the hemostatic valve system 102 and has portions 185 that extend into the chamber 186. The portions 185 advantageously define a surface complimentary to an opposing surface of one or more of the pouches when the pouch is in its expanded configuration. The body 130 includes a tapered portion 140, tubular portion 150, a diverging portion 160, and a housing portion 170. The tapered portion 140 and tubular portion 150 are disposed at the distal end 106 of the hemostatic valve system 102 and have portions adapted to be attached to the proximal end of the elongate tubular member 110. The wall 184 defines multiple device ports 190, two inflation ports 192, and one flush port 194 that extend through the wall 184 and provide access to the chamber 186. While the illustrated hemostatic valve system 102 includes multiple device ports 190, two inflation ports 192, and one flush port 194, any suitable number of ports can be included, and skilled artisans will be able to select an appropriate number of ports for inclusion in a hemostatic valve system or medical device according to a particular embodiment based on various considerations, including the intended use of the hemostatic valve system and/or medical device, the expected number of interventional devices that will be used with the hemostatic valve system and/or medical device, and a desired number of additional or backup ports. Examples of suitable numbers of ports include one, two, three, four, five, six and any other number determined suitable for a particular application.

The tapered portion 140 is disposed on the distal end 106 of the body 130 and extends from the distal end 106 to a second proximal end 142 proximal to distal end 106. The tapered portion 140 comprises a first outer diameter 144, a second outer diameter 146, and a first inner diameter 148. The first outer diameter 144 is disposed on distal end 106 and the second outer diameter 146, which is greater than the first outer diameter 144, is disposed at the second proximal end 142. The first outer diameter 144 gradually increases to the second outer diameter 146, defining tapered portion 140. The first inner diameter 148 is substantially constant through tapered portion 140 and forms lumen 149 that is centered longitudinally along the longitudinal axis 108.

The tubular portion 150 extends from the second proximal end 142 to a third proximal end 152 proximal to the second proximal end 142. The tubular portion 150 comprises a third outer diameter 154 and a second inner diameter 156. The third outer diameter 154 is substantially constant and equal to the second outer diameter 146. The second inner diameter 156 is substantially constant through the tubular portion 150 and equal to the first inner diameter 148. The second inner diameter 156 forms lumen 159 that is centered longitudinally along the longitudinal axis 108.

The diverging portion 160 extends from the third proximal end 152 to a fourth proximal end 162 proximal to the third proximal end 152. The diverging portion 160 comprises first 163, second 164, third 165, and fourth 166 sides. The first 163 and second 164 sides are opposably positioned across the longitudinal axis 108 and extend away from the longitudinal axis 108 from the third proximal end 152 to the fourth proximal end 162. The third 165 and fourth 166 sides are opposably positioned across the longitudinal axis 108 and extend parallel to the longitudinal axis 108 from the third proximal end 152 to the fourth proximal end 162.

The housing portion 170 extends from the fourth proximal end 162 to proximal end 104 of the hemostatic valve system 102. The housing portion 170 comprises first 171, second 172, third 173, and fourth 174 sides. The first 171 and second 172 sides are opposably positioned across the longitudinal axis 108 and extend proximally from the first 163 and second 164 sides of the diverging portion 160. The first 171 and second 172 sides of the housing portion 170 extend away from the longitudinal axis 108 to a fifth proximal end 175 where the first 171 and second 172 sides extend proximally substantially parallel to a first plane that contains the longitudinal axis 108 and is substantially perpendicular to the third 165 and fourth 166 sides of the diverging portion 160. The third 173 and fourth 174 sides of the housing portion 170 are opposably positioned across the longitudinal axis 108 and extend proximally from the third 165 and fourth 166 sides of the diverging portion 160. The third 173 and fourth 174 sides are perpendicular to the first plane and comprise first outwardly curved surfaces 176 and second inwardly curved surfaces 177. The first outwardly curved surfaces 176 extend away from the longitudinal axis 108 and have a first radius. The second inwardly curved surfaces 177 extend proximally from the first outwardly curved surfaces 176 towards the longitudinal axis 108 and have a second radius. The second inwardly curved surfaces 177 converge distal to a peak 178 defined by the second radius of the second inwardly curved surfaces 177 along a second plane that contains the longitudinal axis 108 and is substantially perpendicular to the first plane, defining a recess 179 within the proximal end 104 of the body 130.

Four device ports 190 are disposed linearly on the proximal end 104 of the body 130 within recess 179 and extend through the wall 184 providing access to chamber 186. The device ports 190 are isolated from one another, separated equidistantly and centered along the second plane. While the device ports 190 have been illustrated as located on the proximal end 104 of the body 130, the device ports can be located at any suitable location on the body 130, and skilled artisans will be able to select an appropriate location on the body 130 according to a particular embodiment based on various considerations, including the intended use of the hemostatic valve system and/or medical device, and the expected number of interventional devices that will be used with the hemostatic valve system and/or medical device.

The body 130 can be made of any suitable material, can have various structural configurations, sizes, arrangements, thicknesses, and can be manufactured in any suitable manner. A skilled artisan will be able to select suitable sizes, arrangements, thicknesses, structures, and methods of manufacture based on various considerations, such as the environment in which the device is intended to be used, the type of procedure being performed, and others. For example, body 130 can be formed through the process of injection molding, or any other method of manufacture that can form plastic, metal, or the like. Example materials which can be used to manufacture body 130 include biocompatable materials, metals, plastics, and the like. Each portion of body 130 can be integrally formed or comprise separate elements that can be connected to one another using one or more connections, or means thereof, such as compression fittings, gaskets, snap fitting, adhesives, and the like.

The elongate tubular member 110 defines lumen 111 which extends the entire length of the elongate tubular member 110 from a proximal end permanently or removably connected to the distal end 106 of the body 130, to a distal end. The length of the elongate tubular member 110 can vary depending on the application or procedure being performed. The elongate tubular member 110 can comprise openings at the proximal and distal ends providing access to the lumen 111. The lumen 111 is in communication with lumen 149 of the tapered portion 140, lumen 159 of the tubular portion 150, and chamber 186. The elongate tubular member 110 can comprise any suitable apparatus capable of aiding with the insertion of one or more interventional devices. For example, the elongate tubular member can comprise a dilator, introducer, sheath, or another suitable structure.

Figure 4:
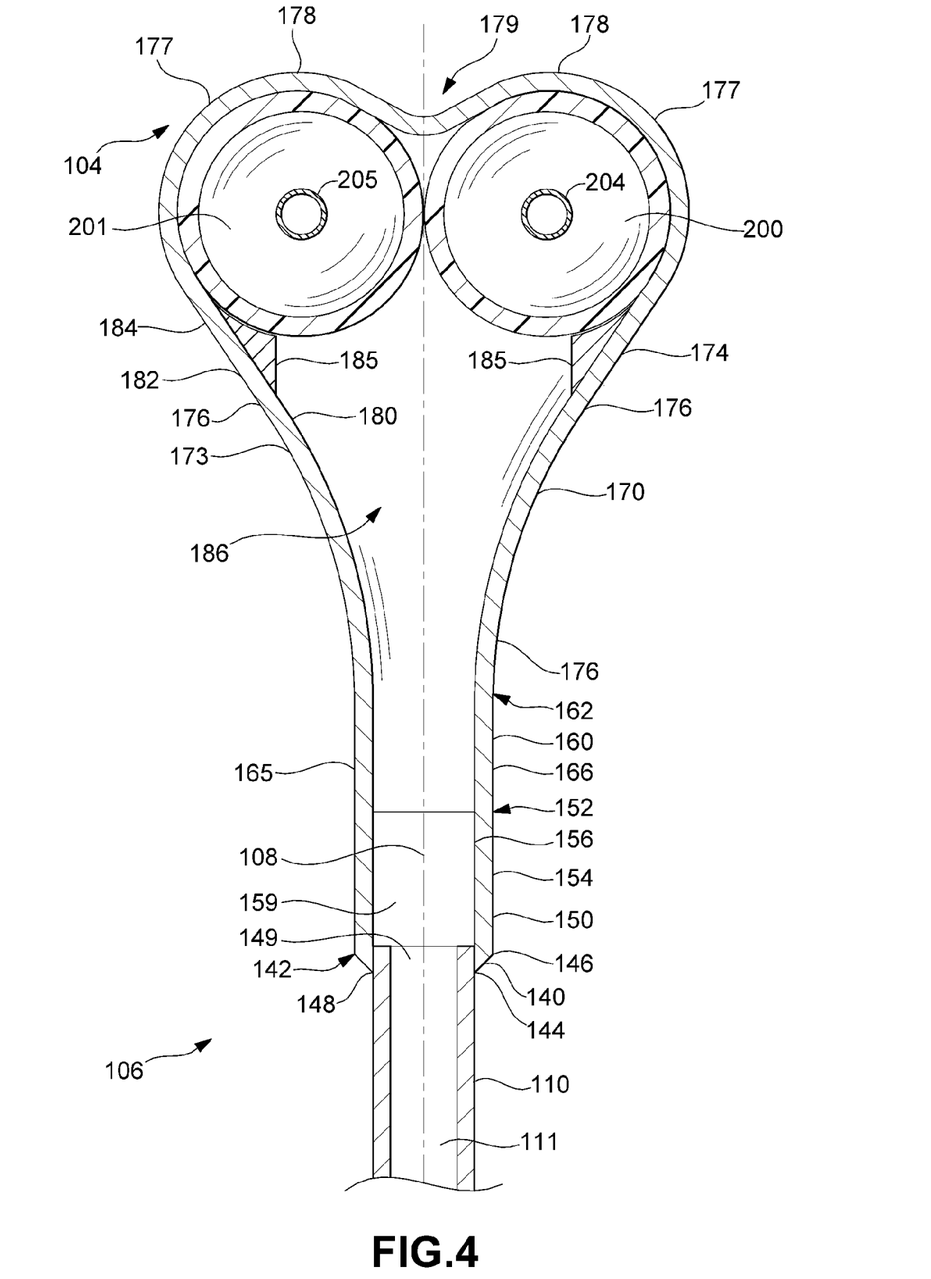
FIG. 4 is a sectional view of the medical device illustrated in FIG. 1, taken along line 4-4 in FIG. 2.
Figures 5, 6:
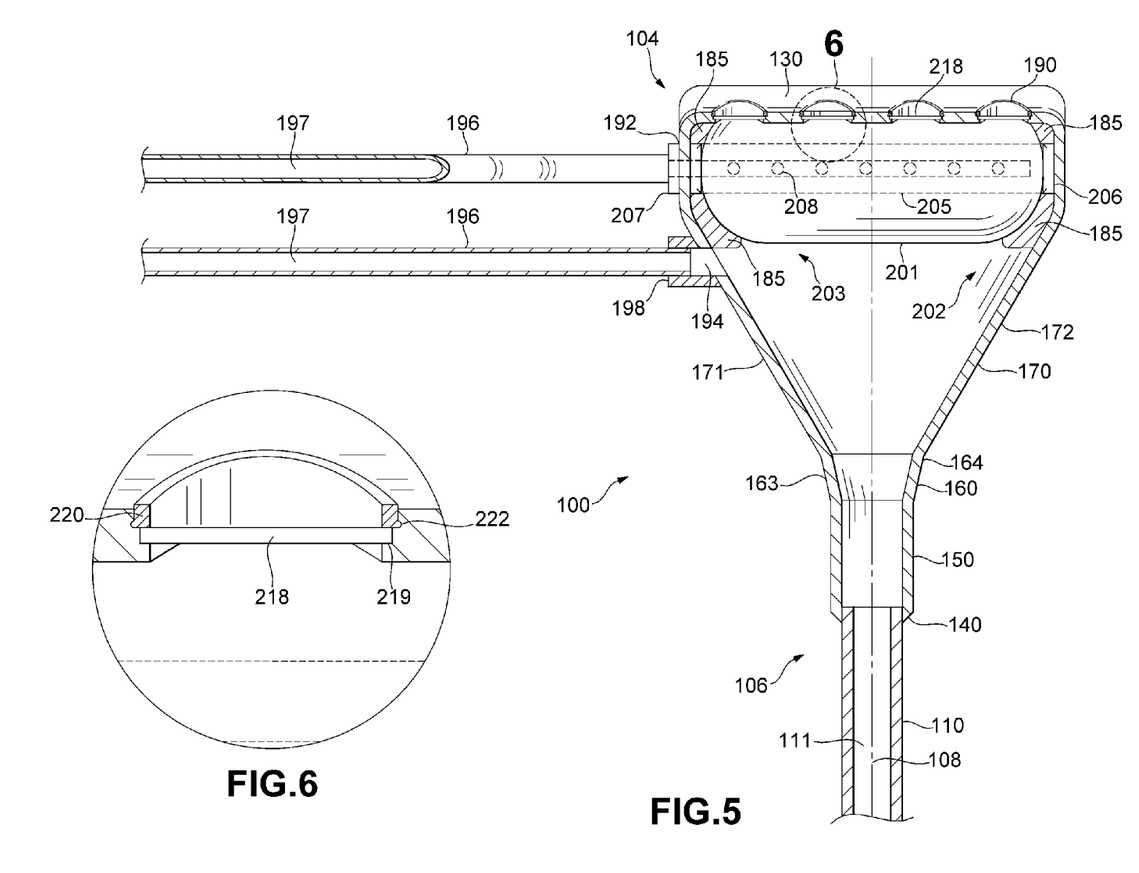
FIG. 5 is a cross-sectional view of the medical device illustrated in FIG. 1, taken along line 5-5 in FIG. 3.
FIG. 6 is a magnified view of the area indicated in FIG. 5.

Diposed within the chamber 186 are two pouches 200, 201 which have first ends 202 and second ends 203. The pouches 200, 201 have a first unexpanded configuration and a second expanded configuration. The pouches 200, 201 are disposed longitudinally substantially parallel to the second plane and expand radially outward advancing from the first unexpanded configuration to the second expanded configuration opposing one another. In the expanded configuration, the pouches 200, 201 coapt along a plane that contains a portion of the access provided by the device ports 190. Alternatively, in the expanded configuration, the pouches 200, 201 coapt along the second plane containing the center of the device ports 190. In the expanded configuration, the pouches 200, 201 create a seal (e.g., hemostatic seal) that adapts to the profiles of the devices inserted through the hemostatic valve system 102 and/or medical device 100. Portions 185 of the body 130 are configured to extend into the chamber 186 and mirror the second expanded configuration of the pouches 200, 201 to substantially limit the flow of fluid between the pouches 200, 201 and the body 130.

Inner shafts 204, 205 extend through apertures located at the first 202 and second ends 203 of the pouches 200, 201 and comprise tubular members, made of a rigid material, such as a polycarbonate, nylon, or polyurethane. The inner shafts 204, 205 have first blind ends 206 and second ends 207. The pouches 200, 201 are bonded to the shafts 204, 205 at the first 202 and second ends 203 using medical grade adhesive. The inner shafts 204, 205 advantageously provide additional support to the pouches 200, 201 and protrude on both ends 202 and 203 of the pouches 200, 201 a distance sufficient to seat the inner shafts 204, 205 in circular recesses in the wall of the body between the portions 185 of the body 130 that mirror the configuration of the pouches 200, 201. In addition, the second ends 207 partially extend out of the inflation ports 192 and are bonded to the inflation ports 192 with medical grade adhesive The second ends 207 are in communication with tubular members 196 which are fixedly attached to the inner shafts 204, 205. The tubular members 196 can be, however, integrally formed with the inner shafts 204, 205, or releasably attached to inner shafts 204, 205 using any suitable means, such as heat bonding or using a coupler, valve, clamp, compression fitting, flexible connector, or other means of connecting. The inner shafts 204, 205 include multiple ports 208 that allow fluid communication between the inner shafts 204, 205 and the pouches 200, 201. The number of ports 208 and materials used to manufacture the inner shafts 204, 205 can vary, and skilled artisans will be able to select an appropriate number of ports and material for inclusion in the inner shafts according to a particular embodiment based on various considerations, including the expected number of interventional devices that will be used with the hemostatic valve system and/or medical device, and a desired pressure of the pouches, or the hemostatic valve system and/or medical device.

The tubular members 196 introduce a fluid to the pouches 200, 201 through lumen 197 to advance the pouches 200, 201 from a first unexpanded configuration to a second expanded configuration, and remove fluid from the pouches 200, 201 to advance them from the second expanded configuration to the first unexpanded configuration. Fluid can be introduced to, or removed from, the one or more tubular members 196 and pouches 200, 201 via a syringe, pump, or other device which can transfer fluid. The tubular members 196 can include an inflation gauge to observe the pressure associated with the expansion and contraction of the pouches 200, 201. Saline can be used to expand the pouches 200, 201 from the first unexpanded configuration to the second expanded configuration. However, other fluids, such as oxygen, air, gel, water, or other compressible materials can be used. The volume of fluid can be measured to determine the amount of expansion the pouches 200, 201 will generate. A skilled artisan will be able to select an appropriate compressible material, amount of compressible material, and a device to introduce said material into the pouches 200, 201 based on various considerations, including the intended use of the hemostatic valve system and/or medical device, the expected number pouches that will be used with the hemostatic valve system and/or medical device, and a desired pressure rating of the pouches, or the hemostatic valve system and/or medical device.

While the illustrated hemostatic valve system 102 includes two pouches 200, 201, any suitable number of pouches can be included, and skilled artisans will be able to select an appropriate number of pouches for inclusion in a hemostatic valve system or medical device according to a particular embodiment based on various considerations, including the intended use of the hemostatic valve system and/or medical device, the expected number of interventional devices that will be used with the hemostatic valve system and/or medical device, the number of ports, and a desired pressure of the pouches, or the hemostatic valve system and/or medical device. Examples of suitable numbers of pouches include one, two, three, four, five, six, seven, eight and any other number determined suitable for a particular application. It is considered advantageous to include an even number of pouches to provide a hemostatic seal forming around the devices traversing the hemostatic valve system 102 and/or medical device 100.

Figure 7:
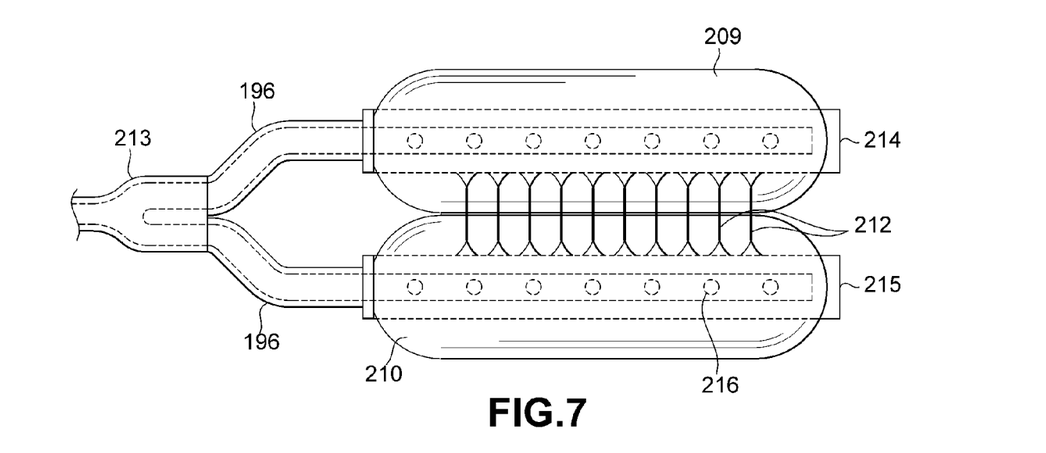
FIG. 7 is a top view of another exemplary pair of pouches in communication with a pair of tubular members.

An exemplary pair of pouches 209, 210 defining a plurality of pleats 212 are illustrated in FIG. 7. The pleats 212 form to the geometry of the devices inserted through the hemostatic valve system 102 and/or medical device 100. The pleats 212 can be constructed by overlapping the pouch 200, 201 material, or adding additional material to the pouch 200, 201 at one or more selected points on the pouch 200, 201 (e.g., the pleats 212 can be located at or near the access provided by the device ports 190). Two tubular members 196 are in communication with two inner shafts 214, 215 which include multiple ports 216. The inner shafts 214, 215 extend through the pouches 209, 210. The ports 216 are in communication with, and provide fluid to, the pouches 209, 210. A manifold 213 connects the tubular members 196 to a single tubular member. Alternatively, if the inner shafts 214, 215 are manufactured from a semi-rigid or flexible material, the inner shafts 214, 215 can extend out of the pouches 209, 210 and connect to the manifold 213.

While the illustrated pouches 209, 210 include multiple pleats 212, any suitable number of pleats can be included, and skilled artisans will be able to select an appropriate number of pleats for inclusion in a hemostatic valve system or medical device according to a particular embodiment based on various considerations, including the intended use of the hemostatic valve system and/or medical device, the expected number and size of interventional devices that will be used with the hemostatic valve system and/or medical device, the number of ports, and a desired pressure of the pouches, and the hemostatic valve system and/or medical device.

The pouches can be inserted prior to finalizing assembly of the medical device 100, or can be inserted subsequent to assembly through the device ports 190, inflation ports 192, flush ports 194, or other accesses as described herein. The pouches can be manufactured as thin-film balloons, bladders, bags, or membranes made of polytetrafluoroethylene (PTFE), nylon, rubber or any other suitable expandable, stretchable, elastic, resilient, or flexible material. The pouches can comprise a single piece, or multiple pieces, of material formed into a suitable shape which can advance from an unexpanded to an expanded configuration. The pouches can have any wall thickness, and skilled artisans will be able to select a suitable wall thickness according to a particular embodiment based on various considerations, including the intended use of the medical device 100, the devices traversing the pouches the desired pressure rating of the hemostatic valve system 102, or the desired maximum and minimum pressures of the pouches. A skilled artisan will be able to select suitable sizes, arrangements, structures and methods of manufactures based on various considerations, such as the environment in which the device is intended to be used, the type of procedure being performed, and others.

A disk 218 is disposed in each device port 190 within a recess 219 in wall 184 and is sized to span the access provided by the device port 190. Recess 219 is configured to mirror the perimeter of the disk 218. The recess 219 has a depth equal to, greater than, or less than, a portion of a perimeter of the disk 218 which is inserted into the recess 219 and secured therein by a retaining ring 220. The retaining ring 220 is installed in a groove 222 in wall 184 located proximal to the recess 219 and is elastic in nature so that it made be deformed and place within groove 222. The groove 222 is configured to mirror a portion of the perimeter of the retaining ring 220. Each disk can be releasably connected, or permanently affixed within the recess 219. For example, an adhesive can be used in combination with the retaining ring 220.

Each disk 218 can form a basin-shaped depression, or can be flat, concave or convex in nature. The disks 218 can be composed of a soft, semi-rigid, or elastic material that is able to provide sufficient flexibility and resilience to devices inserted through the disks 218, to stretch to the extent required to allow a device to traverse the disk 218, and to enable the opening created by the device to substantially return to a pre-stretched condition when the device is removed. In an exemplary embodiment, the disks 218 are made of silicone. Examples of materials that are currently considered suitable include elastomers, ePFTE, nylon, polyethylene, silicon, urethane, and other polymeric materials. The disks 218 can have any suitable configuration, including round, square, or any other configuration that is substantially similar to, or compatible with, the device ports 190. The disks 218 can have any suitable thickness, length, width, or diameter, depending on the procedure being performed, the devices traversing the disks 218, and the desired pressure rating of the hemostatic valve system and/or medical device. While the illustrated embodiment includes one disk 218 disposed in each device port 190, any suitable number of disks can be included, and skilled artisans will be able to select an appropriate number of disks, shapes, sizes and characteristics for inclusion in a hemostatic valve system or medical device according to a particular embodiment based on various considerations, including the intended use of the hemostatic valve system and/or medical device, the expected number of interventional devices that will be used with the hemostatic valve system and/or medical device, the number of ports, and a desired pressure of the pouches, or the hemostatic valve system and/or medical device. Examples of suitable numbers of disks include one, two, three, four, five, six, seven, eight, nine, ten, eleven, twelve and any other number determined suitable for a particular application.

Each disk 218 comprises a slit 224 with two edges substantially parallel to one another configured to coapt prior to a device traversing the disk 218. When a device is inserted through the disk 218, the edges of the slits 224 gravitate towards the outer circumference of the device and are biased towards the center of the opening created by the device. In use, the disk 218 acts as a secondary seal to the the pouches 200, 201. For example, if the pouches 200, 201 were to fail (e.g., rupture or fail to properly advance to the second expanded configuration), the disk 218 would provide a secondary seal to prevent or reduce patient blood loss. The slit 224 can be configured in any manner and can have varying shapes (e.g., linear, Y shaped, X shaped, or circular) and depths. The slit 224 can be characterized by a depth that penetrates the disk 218, or does not penetrate the disk 218 and is open to only one surface of the disk 218, requiring the device to puncture the disk 218 before traversing the disk 218. A second slit can be formed on a surface opposite that of a first slit 224 and can be characterized by a depth that will not contact the first slit 224. When a plurality of disks 218 are used to span a device port 190 the disks 218 can be aligned in a manner such that the slits 224 are not in axial alignment with one another. While the illustrated embodiment includes a single slit 224, any suitable number of slits can be included, and skilled artisans will be able to select an appropriate number of slits, shapes, sizes and characteristics for inclusion in a hemostatic valve system or medical device according to a particular embodiment based on various considerations, including the intended use of the hemostatic valve system and/or medical device, the expected number of interventional devices that will be used with the hemostatic valve system and/or medical device, the number of ports, and a desired pressure of the pouches, or the hemostatic valve system and/or medical device. Examples of suitable numbers of slits include one, two, three, four, five, six and any other number determined suitable for a particular application.

Figure 1:
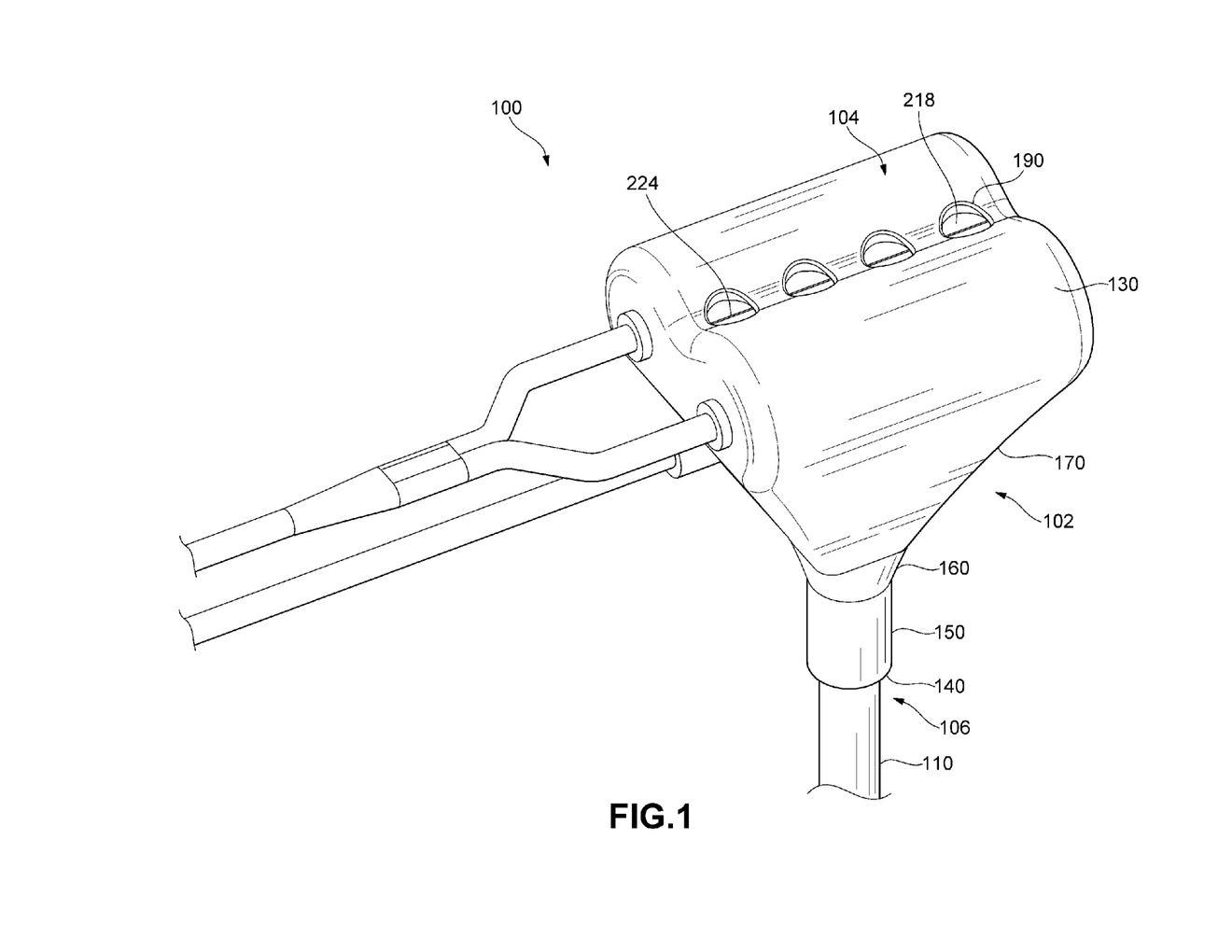
FIG. 1 is a partial perspective view of an exemplary medical device including a hemostatic valve system.
Figure 2:
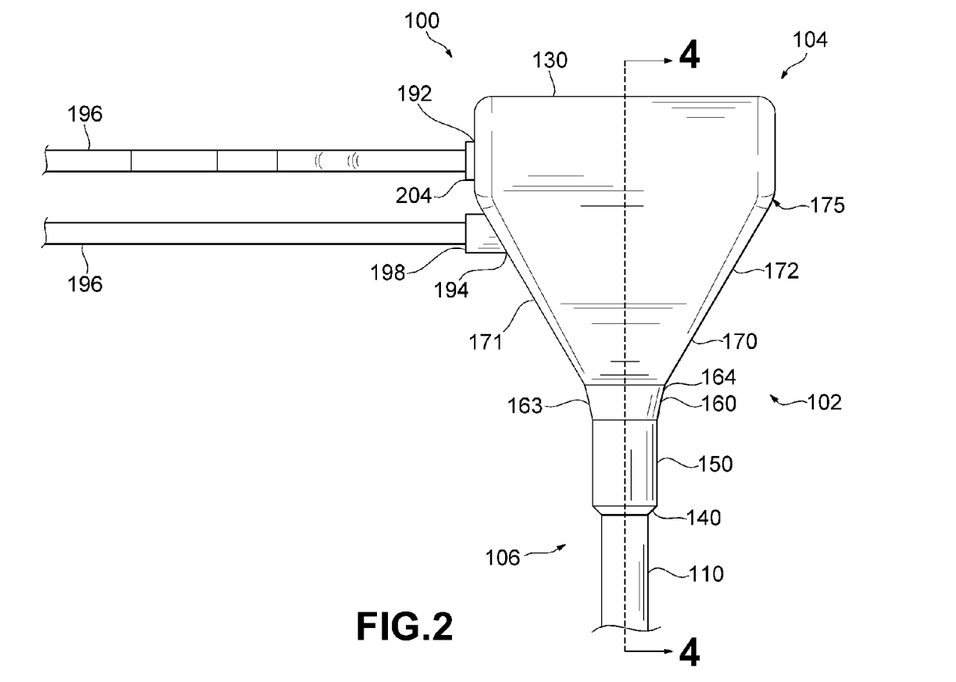
FIG. 2 is an elevation view of the medical device illustrated in FIG. 1.
Figure 3:
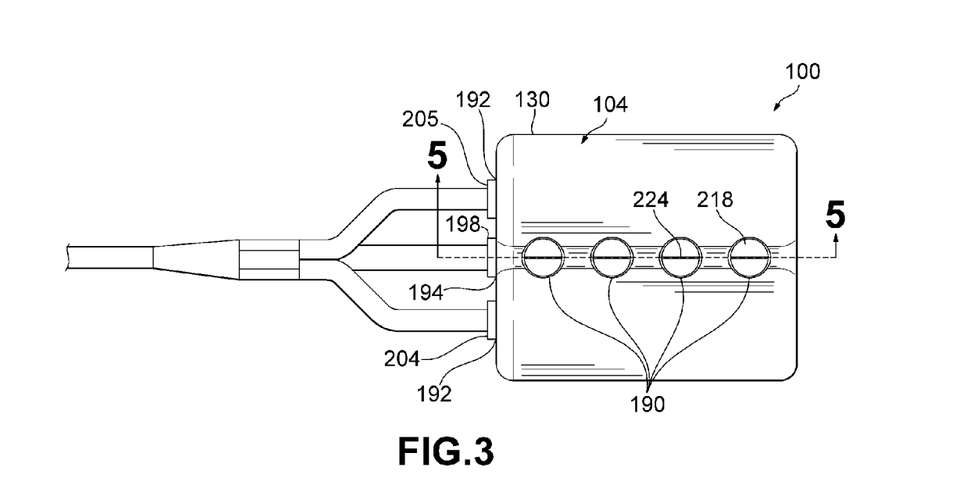
FIG. 3 is a top view of the medical device illustrated in FIG. 1.

A flush port 194 is disposed on the body 130 perpendicular to the device ports 190 and distal to the inflation ports 192. The inflation ports 192 and flush port 194 extend through wall 184 and provide access to the chamber 186. A tubular member 196 is disposed on, and is fixedly attached to, the flush port 194 allowing for flushing and/or removing materials or fluids within the chamber 186. The tubular member 196 can be, however, integrally formed or releasably attached to the body 130 or flush port 194. When fixedly attached to the body 130 or flush port 194, the tubular member 196 is in communication with the chamber 186 via a connection device 198, such as a coupler, valve, or other means for connecting. The flushing and/or removal of the material within the chamber 186 can be accomplished by using a syringe, pump, or other device that has the ability to introduce and/or remove material from the chamber 186 through the tubular members 196. A skilled artisan will be able to select an appropriate device to introduce and/or remove said material into the chamber 186 based on various considerations, including the intended use of the hemostatic valve system and/or medical device.

While the illustrated medical device 100 is illustrated as having the inflation ports 192 and flush ports 194 as located distal to the device ports 190, the ports can be located at any suitable location on the body 130, and skilled artisans will be able to select an appropriate location on the body 130 according to a particular embodiment based on various considerations, including the intended use of the hemostatic valve system and/or medical device, the expected number of interventional devices that will be used with the hemostatic valve system and/or medical device, and the desired number of additional or backup ports. Furthermore, the device ports 190, inflation ports 192, and flush port 194 can comprise any geometric shape, such as a circle, rectangle, triangle, square, etc., and can comprise any length, width, depth, or diameter. Furthermore, the device ports 190, inflation ports 192, and flush port 194 can be configured to have any type of interior or exterior edge, such as a rounded, squared, or chamfered, and can be configured linearly, or non-linearly along any portion of the body 130.

In addition, while the illustrated embodiment includes one or more tubular members used in conjunction with the inflation ports 192 and flush ports 194, any suitable number of tubular members can be included, and skilled artisans will be able to select an appropriate number of tubular members for inclusion in a hemostatic valve system or medical device according to a particular embodiment based on various considerations, including the intended use of the hemostatic valve system and/or medical device, the expected number pouches that will be used with the hemostatic valve system and/or medical device, and the number of ports.

Figure 8:
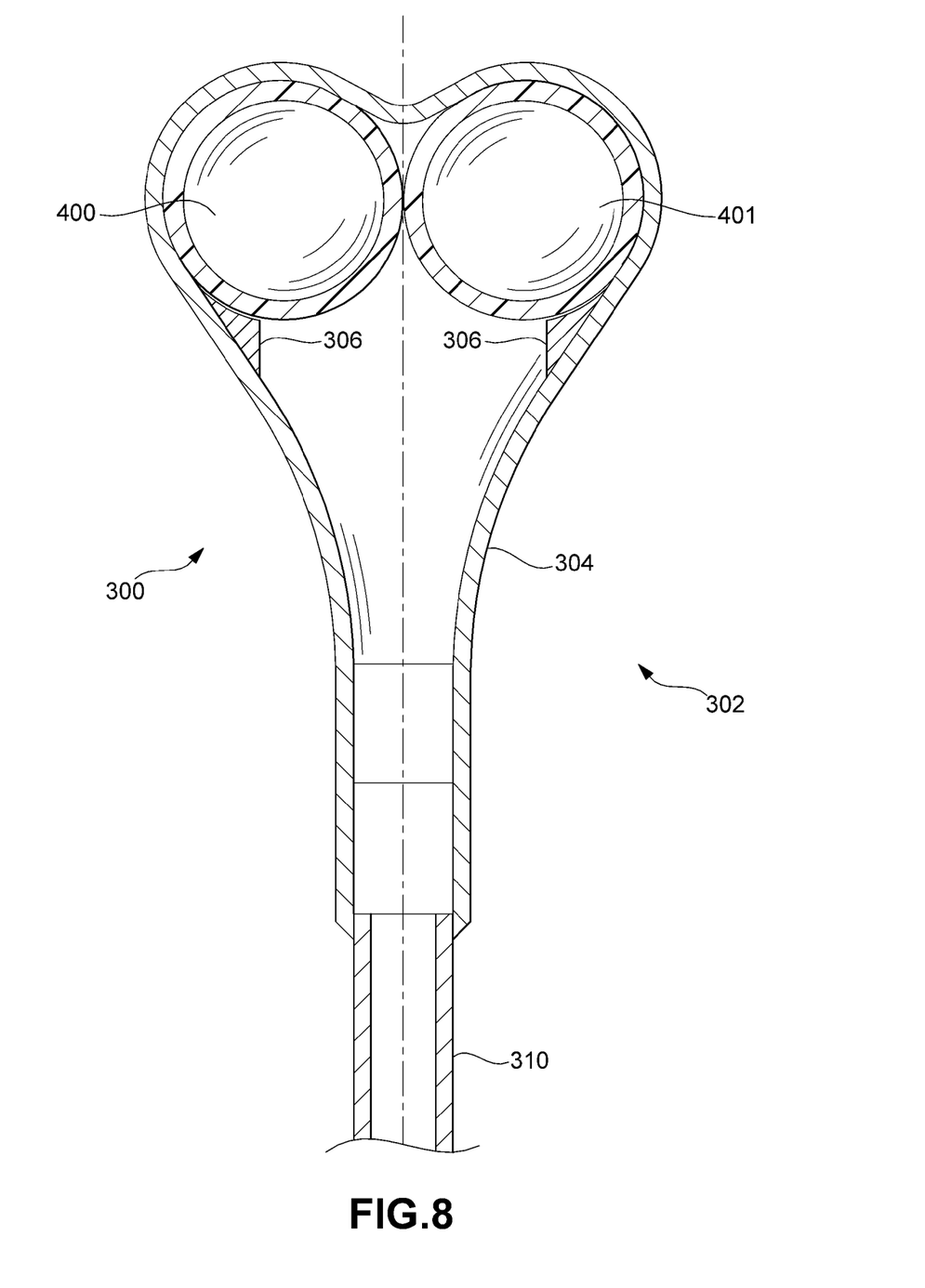
FIG. 8 is a sectional view of the medical device illustrated in FIG. 1, takend along line 4-4 in FIG. 2, with another exemplary pair of pouches.
Figures 9, 10:
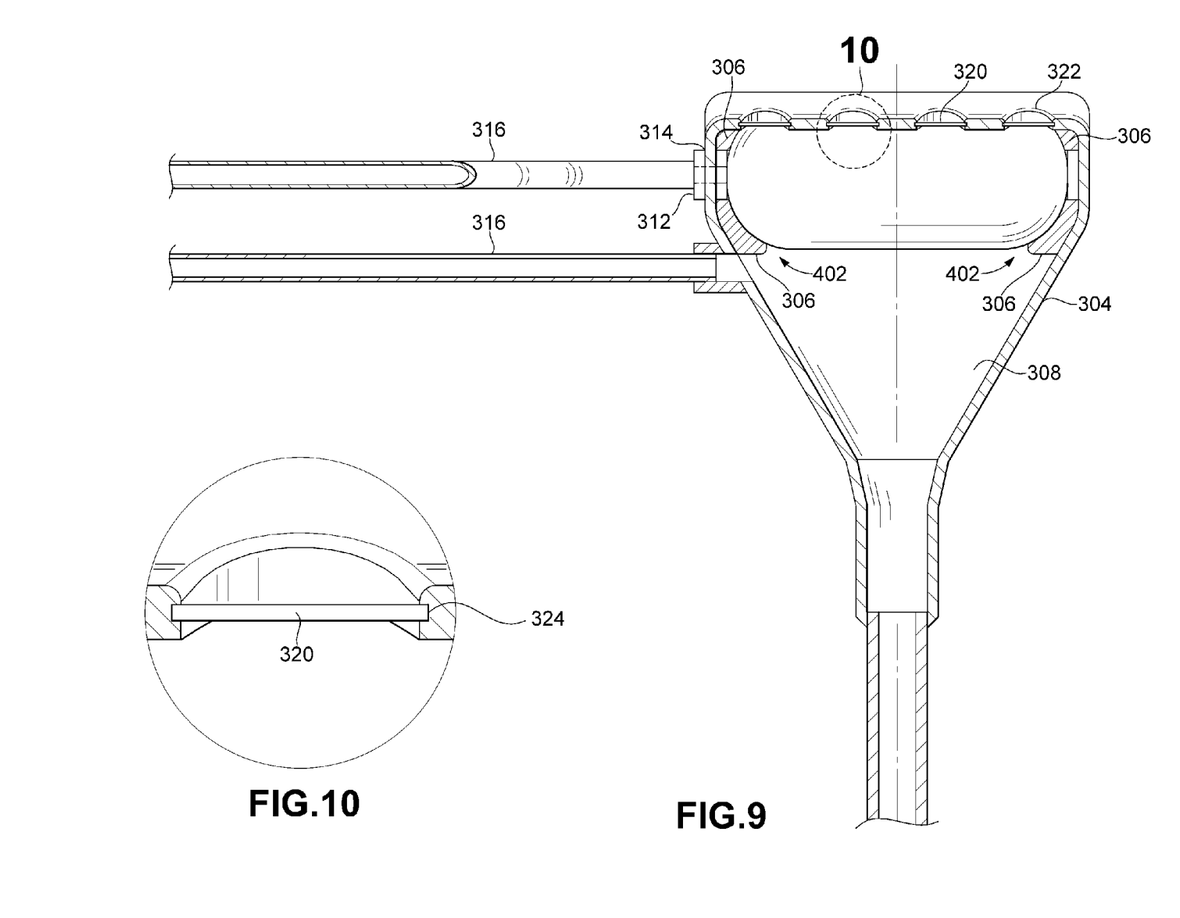
FIG. 9 is a cross-sectional view of the medical device illustrated in FIG. 1, taken along line 5-5 in FIG. 3, with the exemplary pair of pouches illustrated in FIG. 8.
FIG. 10 is a magnified view of the area indicated in FIG. 9.
Figure 11:
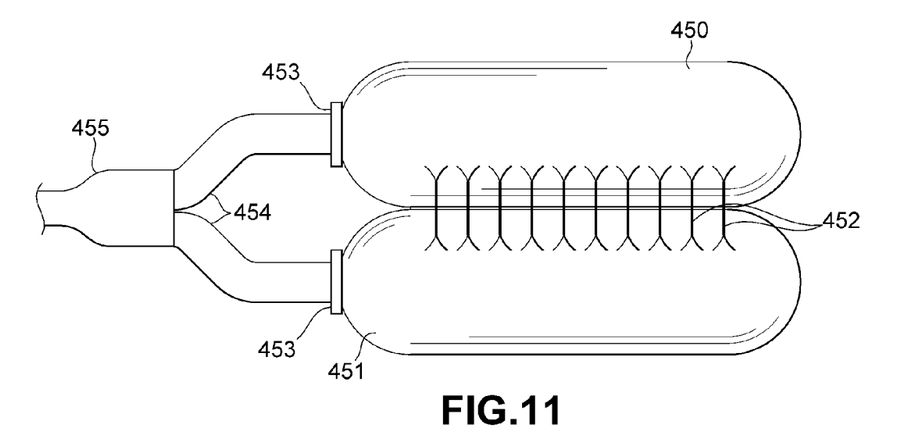
FIG. 11 is a top view of another exemplary pair of pouches in communication with a pair of tubular members.

FIGS. 8 through 10 illustrate another exemplary pair of pouches disposed within the medical device illustrated in FIG. 1. The medical device 300 comprises a hemostatic valve system 302 and an elongate tubular member 310. The second exemplary medical device 300 has two pouches 400, 401 which have first ends 402 and second ends 404. Portions 306 of the body 304 are configured to extend into the chamber 308 and mirror the second expanded configuration of the pouches 400, 401 to substantially limit the flow of fluid between the pouches 400, 401 and the body 304. The first ends 402 of the pouches 400, 401 are affixed to an interior portion of the body 304 of the hemostatic valve system 302 using medical grade adhesive. The second ends 404 of the pouches 400, 401 are affixed to connection devices 312 using medical grade adhesive. The second ends 404 of the pouches 400, 401 include apertures in communication with the connection devices 312 which are fixedly attached to the inflation ports 314. The connection devices 312 can be, however, integrally formed or releasably attached to the inflation ports 314. Two tubular members 316 are in communication with the connection devices 312 and provide fluid to the pouches 400, 401 through lumen 318. The tubular members 316 are disposed on, and are fixedly attached to, the connection devices 312. The tubular members 316 can be, however, integrally formed or releasably attached to the connection devices 312. The connection devices 312 can include any suitable means for connecting the pouches to the tubular members, such as a coupler, valve, clamp, compression fitting, flexible connector, or the like. Skilled artisans will be able to select an connection device 312 according to a particular embodiment based on various considerations, including the intended use of the hemostatic valve system and/or medical device, the size and location of the inflation ports and the connection devices, and the desired number of additional or backup ports.

A disk 320 is disposed in each device port 322 within a track 324 and is sized to span the access provided by the device port 322. The track 324 is defined by a recess in the body 304 and is configured to mirror the perimeter of the disk 320. The track 324 has a depth equal to, greater than, or less than, a portion of a perimeter of the disk 320 which can be inserted into the track 324 and releasably, or permanently, affixed therein via compression fitting, adhesive, retaining ring, or other means.

Another exemplary pair of pouches 450, 451 defining a plurality of pleats 452 are illustrated in FIG. 10. The pouches 450, 451 do not include inner shafts, rather, the pouches 450, 451 are connected at one end to a connection device 453. Two tubular members 454 are in communication with the two connection devices 453 and provide fluid to the pouches 450, 451. A manifold 455 connects the tubular members 454 to a single tubular member.

Figure 12:
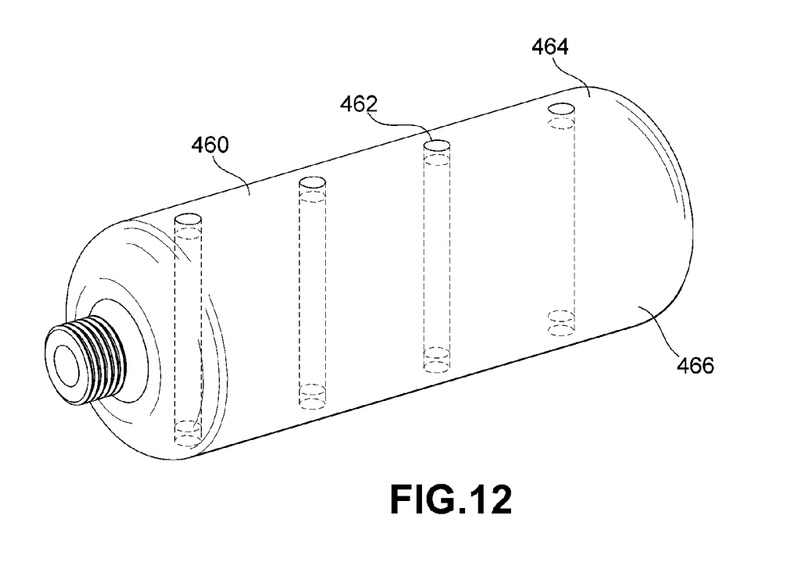
FIG. 12 is a perspective view of another exemplary pouch.

Another exemplary pouch 460 comprising one or more apertures 462 is illustrated in FIG. 12. The apertures 462 extend through the top 464 of the pouch 460 to the bottom 466 of the pouch. When disposed within the chamber of the body, the apertures are in communication with the portions of the body of the hemostatic valve system located distal to the bottom 466 of the pouch 460 (e.g., chamber, diverging portion, tubular portion, tapered portion, and elongate tubular member). The apertures 462 are longitudinally aligned with a portion of the access provided by the device ports. While the illustrated pouch 460 includes multiple apertures 462 extending from the top 464 of the pouch 460 to the bottom 466 of the pouch 460, any suitable number of apertures can be included, and skilled artisans will be able to select an appropriate number of apertures for inclusion in a hemostatic valve system or medical device according to a particular embodiment based on various considerations, including the intended use of the hemostatic valve system and/or medical device, the expected number and size of interventional devices that will be used with the hemostatic valve system and/or medical device, the number of ports, and a desired pressure of the pouches, and the hemostatic valve system and/or medical device. Various configurations of pouches can by used with the hemostatic valve system. For example, the pouches 200, 201, 400, 401, 450, 451, and 460 can include, omit, or combine in any manner, the inner shafts, pleats, and apertures.

Any suitable structure and/or material can be used for the various features described herein, and a skilled artisan will be able to select an appropriate structure and material for the medical device 100 based on various considerations, including the intended use of the medical device 100, the intended arena within which the medical device 100 will be used, the sterilization parameters and/or sterilants to which the medical device 100 is intended to be exposed, and the equipment and/or accessories with which the medical device 100 is intended to be used, among other considerations. Conventional polymeric and metal materials are suitable for use in the various components of the medical device 100. Examples of suitable materials include ePFTE, nylon, polyethylene, and other polymeric materials, extruded or otherwise formed into the desired structures. Materials hereinafter discovered and/or developed that are determined to be suitable for use in the features and elements described herein would also be considered acceptable.

It is noted that all structure and features of the various described and illustrated elements can be combined in any suitable configuration for inclusion in a medical device 100 or hemostatic valve system 102, provided together, or separately. For example, a medical device 100 can comprise a hemostatic valve system and elongate tubular member. The hemostatic valve system comprises a body having one or more device ports, one or more pouches, and one or more disks. Furthermore, the hemostatic valve system can include neither, one, or both of the elongate tubular member and the tubular members. The hemostatic valve system can include tubular members that can be integrally formed with, or releasably attached to, the body, inflation ports, or pouches. When formed or attached to the pouches the tubular members can include a means for sealing the inflation port, such as a gasket. The disks can be affixed to a portion of the interior or exterior surface of the body, the device ports, or the pouches.

An exemplary method of performing a procedure using a medical device 100 having a hemostatic valve system 102 comprises the steps of providing a medical device 100. The medical device 100 comprises a hemostatic valve system 102 and an elongate tubular member 110. The hemostatic valve system 102 comprises a body 130, two pouches 200, 201, and one or more disks 210. The body comprises a proximal end 104 and distal end 106, a chamber 186 disposed between the proximal 104 and distal 106 ends, a wall 184 defining an interior 180 and exterior 182 surface, and a plurality of device ports 190. The plurality of device ports 190 are disposed on the proximal end 104 and extend through the wall 184 providing access to the chamber 186. The pouches 200, 201 are disposed within the chamber 186 and have a first unexpanded configuration and a second expanded configuration. The one or more disks 210 are disposed within a recess 219 of the device ports 190 and are affixed within the recess 219 by a retaining ring 220. A user inserts one or more devices through the medical device 100, traversing the hemostatic valve system 102 and elongate tubular member 110, positioning the devices at a point of treatment. The user advances the pouches 200, 201 to their second expanded configuration prior to, or subsequent to insertion of the one or more devices. The user then provides treatment at a treatment site and removes the devices from the medical device 100. The pouches 200, 201 can then be advanced from the second expanded configuration to the first unexpanded configuration.

The foregoing disclosure includes the best mode of the inventor for practicing the invention. It is apparent, however, that those skilled in the relevant art will recognize variations of the invention that are not described herein. While the invention is defined by the appended claims, the invention is not limited to the literal meaning of the claims, but also includes these variations.

What is claimed is:

1. A medical device for use in inserting an interventional device into the body of a patient, said medical device comprising:

an elongate tubular member having proximal and distal ends and defining a lumen extending between the proximal and distal ends, the elongate tubular member having a longitudinal axis; and a hemostatic valve system disposed on the proximal end of the elongate tubular member, the hemostatic valve system comprising a body having first and second ends, a wall defining an interior chamber and a plurality of device ports extending through the wall and providing access to the interior chamber and the lumen of the elongate tubular member;

first and second inflatable pouches disposed opposite each other within the interior chamber with respect to the longitudinal axis of the elongate tubular member, each of the inflatable pouches defining an interior space and having an unexpanded configuration and an expanded configuration, the first and second inflatable pouches coapting along a plane that contains a portion of each device port of the plurality of device ports when each of the first and second inflatable pouches is in its expanded configuration, the first and second inflatable pouches adapted to form a seal around said interventional device disposed through one of the plurality of device ports; and an inflation tubular member defining an inflation lumen providing fluid access to the interior space of each of the first and second inflatable pouches.

2. The medical device of claim 1, further comprising a sealing member contacting the wall and disposed within one of the plurality of device ports.

3. The medical device of claim 2, wherein the wall defines a recess disposed around one of the plurality of device ports, the sealing member defines a perimeter edge, and the perimeter edge of the sealing member is disposed within the recess.

4. The medical device of claim 3, further comprising a retaining member disposed adjacent the sealing member and configured to retain the perimeter edge of the sealing member in the recess.

5. The medical device of claim 4, wherein the sealing member defines an opening configured to allow passage of said interventional device through the one of the plurality of device ports and to form a second seal around said interventional device.

6. The medical device of claim 2, wherein the sealing member comprises silicone.

7. The medical device of claim 1, wherein each of the first and second inflatable pouches defines a pleat adapted to unfold as the inflatable pouch moves from the unexpanded configuration to the expanded configuration.

8. The medical device of claim 1, wherein the wall defines a flush port providing access to the interior chamber.

9. The medical device of claim 1, wherein the wall has an interior surface having a portion complimentary to an opposing surface of one of the first and second inflatable pouches when the inflatable pouch is in its expanded configuration.

10. A medical device for use in inserting an interventional device into the body of a patient, said medical device comprising:
- an elongate tubular member having proximal and distal ends and defining a lumen extending between the proximal and distal ends and having a longitudinal axis; and
- a hemostatic valve system disposed on the proximal end of the elongate tubular member, the hemostatic valve system comprising
  - a body having first and second ends, a wall defining an interior chamber and a plurality of device ports extending through the wall and providing access to the interior chamber and the lumen of the elongate tubular member;
  - first and second inflatable pouches disposed opposite each other within the interior chamber with respect to the longitudinal axis of the elongate tubular member, each of the inflatable pouches defining an interior space and having an unexpanded configuration and an expanded configuration, the first and second inflatable pouches coapting along a plane that contains a portion of each device port of the plurality of device ports when each of the first and second inflatable pouches is in its expanded configuration, the first and second inflatable pouches adapted to form a seal around said interventional device disposed through one of the plurality of device ports;
  - a sealing member contacting the wall and disposed within one of the plurality of device ports, the sealing member defining an opening configured to allow passage of said interventional device through the one of the plurality of device ports and to form a second seal around said interventional device; and
  - an inflation tubular member defining an inflation lumen providing fluid access to the interior space of each of the first and second inflatable pouches.

11. The medical device of claim 10, wherein the wall defines a recess disposed around one of the plurality of device ports, the sealing member defines a perimeter edge, and the perimeter edge of the sealing member is disposed within the recess.

12. The medical device of claim 11, further comprising a retaining member disposed adjacent the sealing member and configured to retain the perimeter edge of the sealing member in the recess.

13. The medical device of claim 10, wherein the sealing member comprises silicone.

14. The medical device of claim 10, wherein each of the first and second inflatable pouches defines a pleat adapted to unfold as the inflatable pouch pouches moves from the unexpanded configuration to the expanded configuration.

15. The medical device of claim 10, wherein the wall defines a flush port providing access to the interior chamber.

16. The medical device of claim 10, wherein the wall has an interior surface having a portion complimentary to an opposing surface of one of the first and second inflatable pouches when the inflatable pouch is in its expanded configuration.

17. The medical device of claim 10, wherein the wall has an interior surface having a portion complimentary to an opposing surface of one of the first and second inflatable pouches when the inflatable pouch is in its expanded configuration.

18. A medical device for use in inserting an interventional device into the body of a patient, said medical device comprising:
- an elongate tubular member having proximal and distal ends and defining a lumen extending between the proximal and distal ends and having a longitudinal axis; and
- a hemostatic valve system disposed on the proximal end of the elongate tubular member, the hemostatic valve system comprising
  - a body having first and second ends, a wall defining an interior chamber, a plurality of device ports extending through the wall to define an opening providing access to the interior chamber and the lumen of the elongate tubular member, and a plurality of recesses, each recess of the plurality of recesses disposed around one of the plurality of device ports;
  - first and second inflatable pouches disposed opposite each other within the interior chamber with respect to the longitudinal axis of the elongate tubular member, each of the inflatable pouches defining an interior space and having an unexpanded configuration and an expanded configuration, the first and second inflatable pouches coapting along a plane that contains a portion of each device port of the plurality of device ports when each of the first and second inflatable pouches is in its expanded configuration, the first and second inflatable pouches adapted to form a seal around said interventional device disposed through one of the plurality of device ports;
  - a plurality of sealing members, each sealing member of the plurality of sealing members defining a perimeter edge disposed within a recess of the plurality of recesses and an opening configured to allow passage of said interventional device through the device port and to form a second seal around said interventional device, and spanning the opening defined by the device port;
  - a first inflation tubular member defining a first inflation lumen providing fluid access to the interior space of the first inflatable pouch;
  - a second inflation tubular member defining a second inflation lumen providing fluid access to the interior space of the second inflatable pouch; and
  - a manifold defining a master inflation lumen providing fluid access to the first and second inflation lumens.

19. The medical device of claim 18, wherein each of the first and second inflatable pouches defines a pleat adapted to unfold as the inflatable pouch moves from the unexpanded configuration to the expanded configuration.

20. The medical device of claim 18, wherein the wall defines a flush port providing access to the interior chamber.

* * * * *